(12) United States Patent
Voith (10) Patent No.: US 6,731,973 B2
(45) Date of Patent: May 4, 2004

(54) METHOD AND APPARATUS FOR PROCESSING PHYSIOLOGICAL DATA

(75) Inventor: Paul Richard Voith, Milwaukee, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 226 days.

(21) Appl. No.: 09/681,823

(22) Filed: Jun. 12, 2001

(65) Prior Publication Data

US 2002/0188211 A1 Dec. 12, 2002

(51) Int. Cl.[7] .......................................... A61B 5/0452
(52) U.S. Cl. ..................................................... 600/513
(58) Field of Search .................................. 600/509, 513, 600/515, 300–301, 483; 128/920, 923–925

(56) References Cited

U.S. PATENT DOCUMENTS

| | | | | | |
|---|---|---|---|---|---|
| 4,865,043 | A | * | 9/1989 | Shimoni | ...................... 600/513 |
| 5,178,154 | A | * | 1/1993 | Ackmann et al. | ........... 600/526 |
| 5,211,179 | A | | 5/1993 | Haberl et al. | |
| 5,735,286 | A | | 4/1998 | Notton et al. | |

* cited by examiner

Primary Examiner—Kennedy Schaetzle
Assistant Examiner—Kristen Droesch
(74) Attorney, Agent, or Firm—Michael Best & Friedrich LLP (57) ABSTRACT

A method and apparatus for processing physiological data, particularly non-electrocardiogram, cardiac-related data, by identifying the physiological data associated with atypical cardiac cycles.

78 Claims, 8 Drawing Sheets

METHOD AND APPARATUS FOR PROCESSING PHYSIOLOGICAL DATA

BACKGROUND OF INVENTION

The invention relates to a method and apparatus for processing physiological data, particularly non-electrocardiogram, cardiac-related data, by identifying the physiological data associated with atypical cardiac events.

Much of the physiological data which may be recorded from the human body is related to the cardiac cycle. The most obvious example is the electrocardiogram (ECG). Each time the heart beats, the electrical activity of the heart creates electrical potentials which are detectable with electrodes attached to the body surface. The ECG waveform is so dependent upon the cardiac cycle that it is relied upon to provide significant diagnostic information about the health and functioning of the heart. Moreover, differences in the beat to beat function of the heart closely correlate with beat to beat changes in the morphology of the ECG waveform.

In recent years, the manual analysis of the ECG waveform has been enhanced by the use of ECG analysis software algorithms, such as ECG classification engines. ECG classification engines are used to automatically identify and categorize individual heart beats within an ECG waveform stream based on the morphology of the individual heart beats. ECG classification engines are also used to form associations among the individual heart beats having similar morphologies.

To identify and categorize individual heart beats, the ECG classification engine first samples an acquired ECG waveform stream to create ECG data representing the waveform stream. Various filtering techniques may be applied, either before or after sampling the waveform stream, to eliminate noise, such as power line interference.

Once the ECG data is sampled and filtered, the data is divided into segments. Each segment generally represents a single cardiac cycle or heart beat. In order to identify each heart beat, the ECG classification engine locates the QRS complex within each heart beat. Once the ECG data is segmented, each data segment is classified according to the type of heart beat that may have generated the data segment. For example, the data segments may be classified as typical, ventricular, or paced.

It is not uncommon, however, for the ECG classification engine to group the data segments before classifying the data segments. The data segments may be grouped based on the morphology of the ECG data within each data segment. The data segments with similar morphologies are grouped together. In order to group the data segments, each new data segment is compared, in some manner, to a representative data segment from each of the data segment groups. In order to compare each new data segment to the representative data segments, the two data segments must be aligned according to a fiducial point. Typically, the R wave within the QRS complex of each data segment is used as the fiducial point, although any other easily-recognizable feature in the two data segments may be used as the fiducial point.

Once the data segments are grouped, the ECG classification engine can analyze and classify an entire group of data segments by analyzing either one data segment within the group or by analyzing and classifying a representative data segment for the group. The representative data segment for a group of data segments may be, for example, an average of the data segments or the median data segment. The ability to analyze one data segment that represents an entire group of data segments greatly reduces the computational burden on the ECG classification engine and reduces the data storage requirements of the ECG system.

Once the data segments are analyzed and classified based solely upon their morphology, an additional analysis may be performed. Each data segment may be analyzed based on the morphology of adjacent data segments. This additional analysis may lead to a different classification for the data segment or an enhanced classification. For example, a data segment classified as a ventricular contraction (VC) data segment may be classified as a premature ventricular contraction (PVC) data segment if it is sufficiently close to the preceding heart beat. In addition, a sequence of data segments may exhibit a rhythm or an arrhythmia. For example, a series of three or more ventricular contractions at a high rate represents a ventricular tachycardia arrhythmia.

In summary, the ECG classification engine first groups data segments based on the morphology of each individual data segment. Second, the ECG classification engine groups the morphologies into a classification. Third, the ECG classification engine narrows the classification of each individual data segment based on the data segment's relationship to immediately-adjacent data segments. Finally, the ECG classification engine qualifies the classification of each individual data segment based on the sequence of data segments in which each individual data segment is located.

In addition to ECG data, many other types of physiological data are closely related to the cardiac cycle. Non-ECG physiological data closely related to the cardiac cycle includes, for example, continuous blood pressure data, blood oxygen saturation data, cardiac impedance data, cardiac sound data, and cardiac output data. Non-ECG physiological data closely related to the cardiac cycle also includes cardiac imaging data, which is created whenever the heart is imaged with imaging methods such as X-ray, nuclear magnetic resonance (NMR), or scintiphotography.

Similar to the processing of ECG data, non-ECG physiological data from one cardiac cycle is often averaged or otherwise combined with the data obtained during other cardiac cycles in order to enhance the features of the non-ECG physiological data. In order to combine the non-ECG physiological data from several cardiac cycles, the data must be divided into segments by identifying which portion of the data is from one cardiac cycle and which is from another cardiac cycle. Also, in order to combine the data in a coherent manner, the data segments must be aligned so that the same features are being compared in each of the data segments. However, non-ECG physiological data does not generally include a consistent and recognizable fiducial point like the QRS complex of ECG data.

While dividing and aligning ECG data segments is generally straightforward, there can be difficulties when attempting to divide and align non-ECG physiological data segments, because it may be difficult to identify a consistent fiducial point within the data. This problem is often solved by simultaneously acquiring ECG data which may be temporally associated with the non-ECG physiological data. The non-ECG physiological data is then divided into segments and aligned using the QRS complex of the simultaneously-acquired ECG data as a fiducial point. This method of aligning non-ECG physiological data with simultaneously-acquired ECG data is known as R-Wave Gating. A representative non-ECG physiological data segment is then generated by averaging or combining the segments.

However, the representative non-ECG physiological data segment that is generated by averaging all of the non-ECG physiological data segments may not accurately represent the non-ECG physiological data. The combination of segments relies upon the presumption that each segment represents a cardiac cycle substantially similar to the other data segments that it is being combined with. However, atypical and abnormal cardiac cycles may occur periodically while the non-ECG physiological data is being acquired.

An atypical cardiac cycle may be considered a normal cardiac cycle, i.e. a cardiac cycle may be different from other cardiac cycles, but may not be related to a cardiac disease, malfunction, or abnormality. Several types of normal cardiac cycles may exist within a stream of ECG waveform data. However, each of these normal cardiac cycles differs from the typical cardiac cycles and is thus considered atypical. When averaged with typical data segments, atypical data segments, even though they represent a normal cardiac cycle, can have a negative impact on the representative data segment.

Abnormal cardiac cycles are also referred to as ectopic or aberrant heart beats. During an abnormal cardiac cycle, the differing hemodynamic function of the heart results in a significantly distorted data segment in comparison to a typical data segment. For example, when a premature ventricular contraction (PVC) occurs, the associated data segment is significantly distorted in comparison to a data segment associated with a typical cardiac cycle. Thus, one PVC data segment, even when averaged with several typical data segments, can have a significant negative impact on the representative data segment, which is intended to represent the average of the typical data segments. While rare in healthy individuals, abnormal cardiac cycles can occur frequently in patients with poor cardiac functionality, resulting in a distorted and inaccurate representative data segment. In the case of cardiac imaging data, a single abnormal data segment may decrease the effectiveness of the representative data segment, and may even result in expensive re-testing.

SUMMARY OF INVENTION

In light of the limitations described above, a need exists for a method of processing non-ECG physiological data by identifying the non-ECG physiological data associated with atypical or abnormal cardiac cycles, and, preferably, separating the non-ECG physiological data associated with the atypical or abnormal cardiac cycles from the non-ECG physiological data associated with the typical or normal cardiac cycles.

Accordingly, the invention provides a method for processing non-ECG physiological data acquired from a patient. The method includes the acts of acquiring a first type of physiological data and a second type of physiological data from the patient, dividing the first type of physiological data and the second type of physiological data into corresponding segments, analyzing the first type of physiological data segments to determine the morphology of each data segment, clustering the data segments of the first type of physiological data into groups based on the morphology of each data segment, and clustering the data segments of the second type of physiological data into groups based on the corresponding segments of the first type of physiological data.

The invention provides another method of processing physiological data acquired from a patient. The method includes the acts of acquiring electrocardiogram data and non-electrocardiogram physiological data from the patient, dividing the electrocardiogram data and the non-electrocardiogram physiological data into corresponding segments, analyzing the electrocardiogram data segments to identify atypical and typical segments, associating the atypical electrocardiogram data segments with the corresponding non-electrocardiogram physiological data segments, and associating the typical electrocardiogram data segments with the corresponding non-electrocardiogram physiological data segments.

The apparatus is a clinical device that may be connected to a patient. The device includes an acquisition module for acquiring ECG data and non-ECG physiological data from the patient. The device also includes software, such as an ECG classification engine, for dividing the ECG data and the non-ECG physiological data into segments and for analyzing the ECG data segments to identify atypical and typical segments. The software also associates the atypical ECG data segments with the corresponding non-ECG physiological data segments and associates the typical ECG data segments with the corresponding non-ECG physiological data segments. The software may also separate the data segments, align the separated data segments, and generate representative data for the separated data segments. The clinical device may be coupled to a display monitor for displaying the representative data to a clinician. Also, the clinical device may be coupled to a transmitter in order to transmit the representative data to a remote location.

Various other features and advantages of the invention are set forth in the following drawings, detailed description, and claims.

DETAILED DESCRIPTION

Before one embodiment of the invention is explained in full detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including" and "comprising" and variations thereof herein is meant to encompass the items listed thereafter and equivalents thereof as well as additional items.

Figure 1:
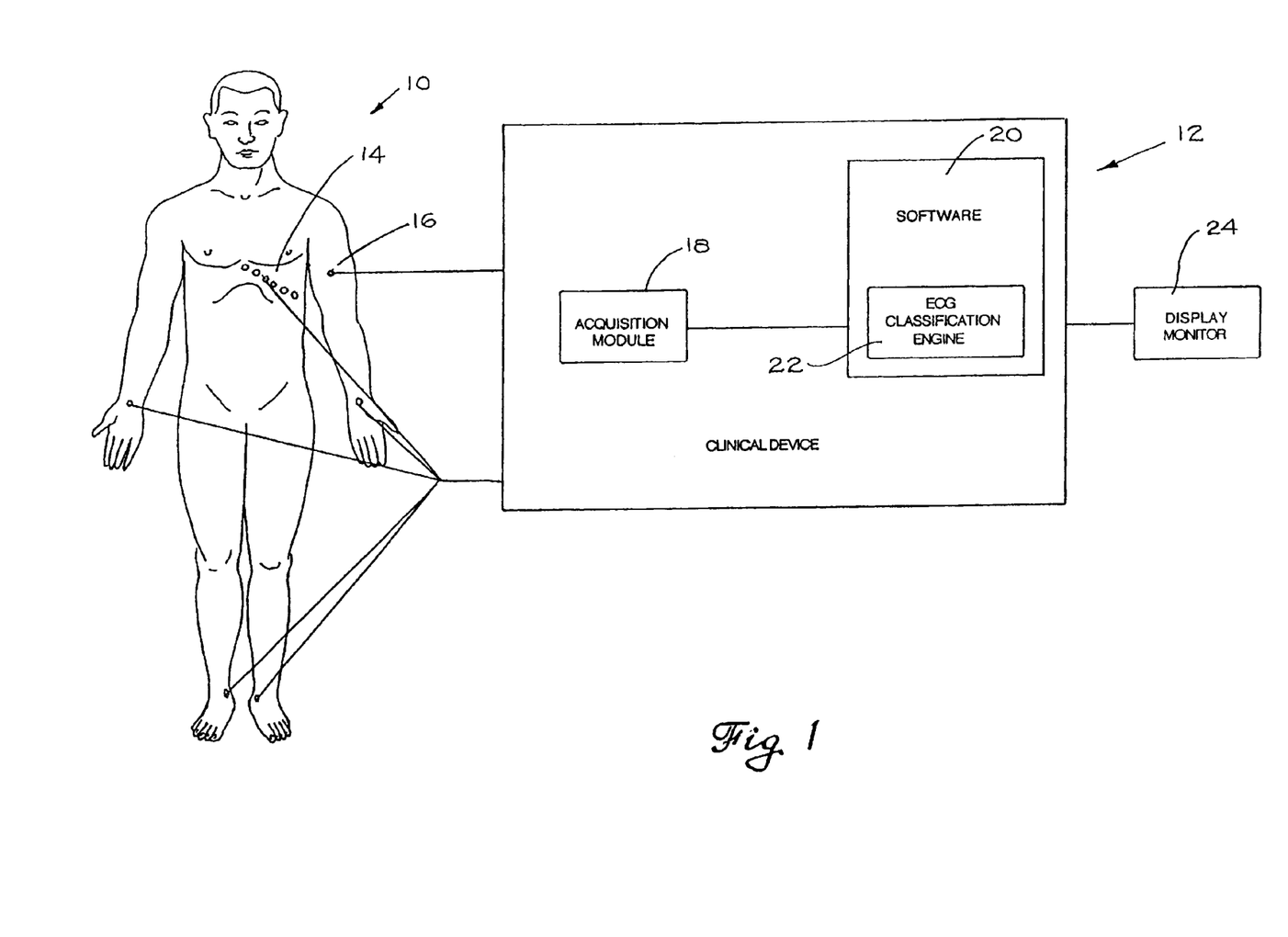
FIG. 1 illustrates the apparatus embodying the invention.

FIG. 1 illustrates a clinical device 12 embodying the invention. As is known in the art, the clinical device 12 is connected to a plurality of electrodes 14 attached to a patient 10 to acquire ECG data from the patient 10. Preferably, the clinical device 12 is also coupled to at least one sensor or transducer 16 for acquiring any type of non-ECG physiological data. The non-ECG physiological data may include continuous blood pressure data, blood oxygen saturation data, cardiac impedance data, cardiac sound data, cardiac output data, or any other physiological data. Alternatively or in addition to being coupled to at least one sensor or transducer 16, the clinical device 12 may acquire non-ECG physiological data by being coupled to a cardiac imaging device (not shown), such as an X-ray device, an NMR device, a scintiphotography device, or any other diagnostic medical device.

The clinical device 12 includes an acquisition module 18 coupled to the plurality of electrodes 14 and the sensor or transducer 16, and software 20 coupled to the acquisition module 18. The software 20 includes an ECG classification engine 22. A suitable ECG classification engine is EKPro developed by GE Medical Systems Information Technologies, Inc.

The clinical device 12 may be coupled to a display monitor 24 for displaying representative data to a clinician. The clinical device 12 may also be coupled to a transmitter (not shown) for transmitting the representative data to a remote location.

Figure 2A:
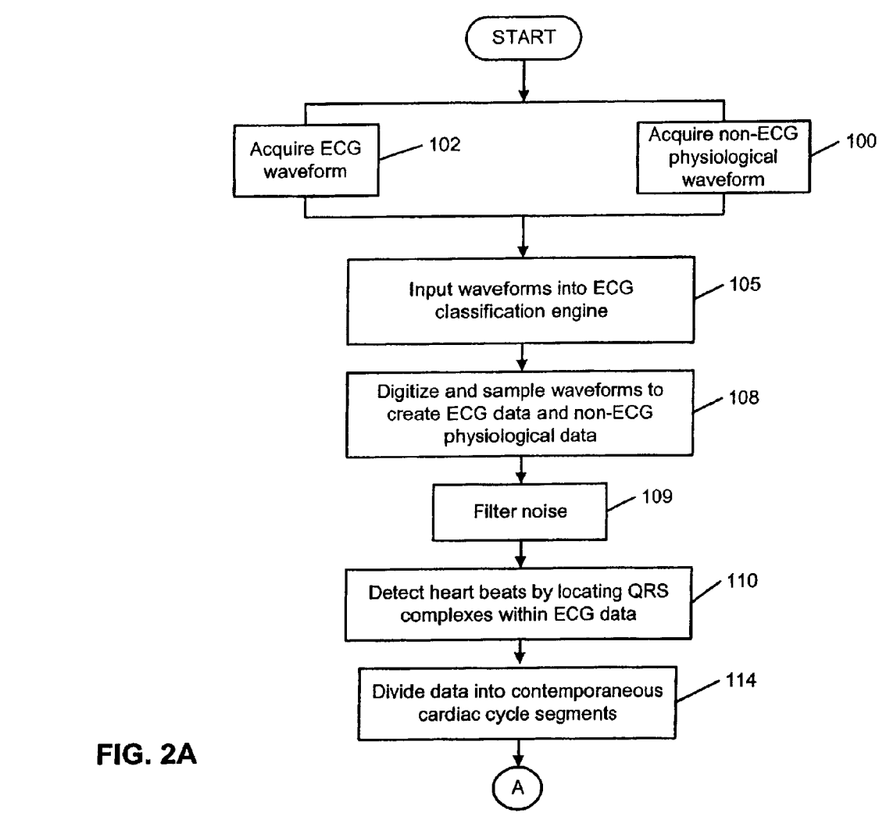
FIGS. 2A, 2B, and 2C illustrate the method embodying the invention.
Figure 2B:
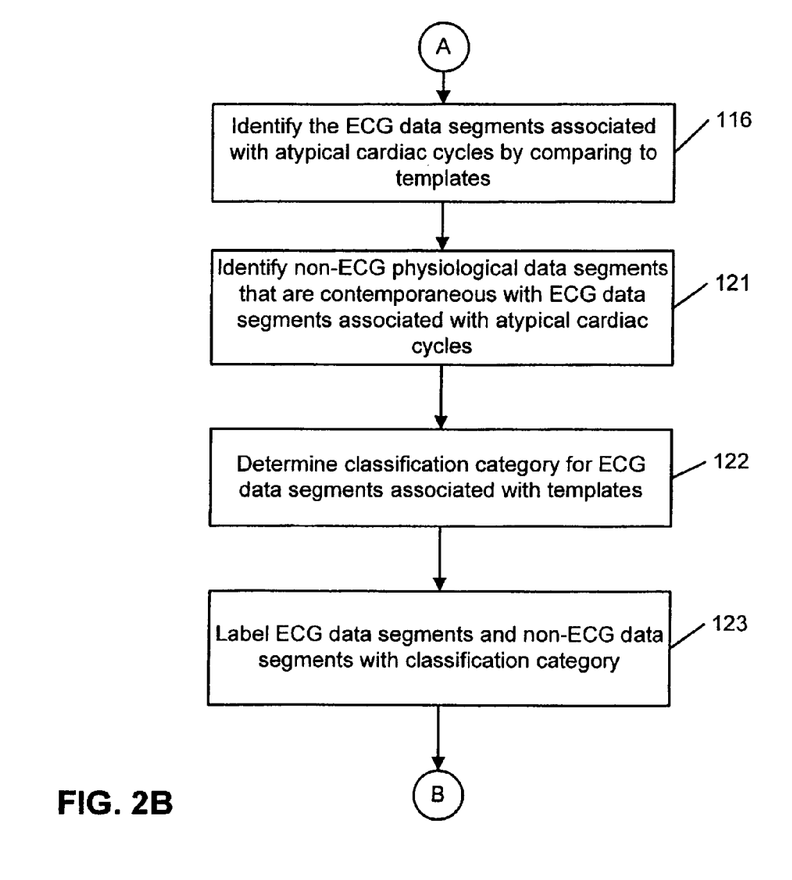
Figure 2C:
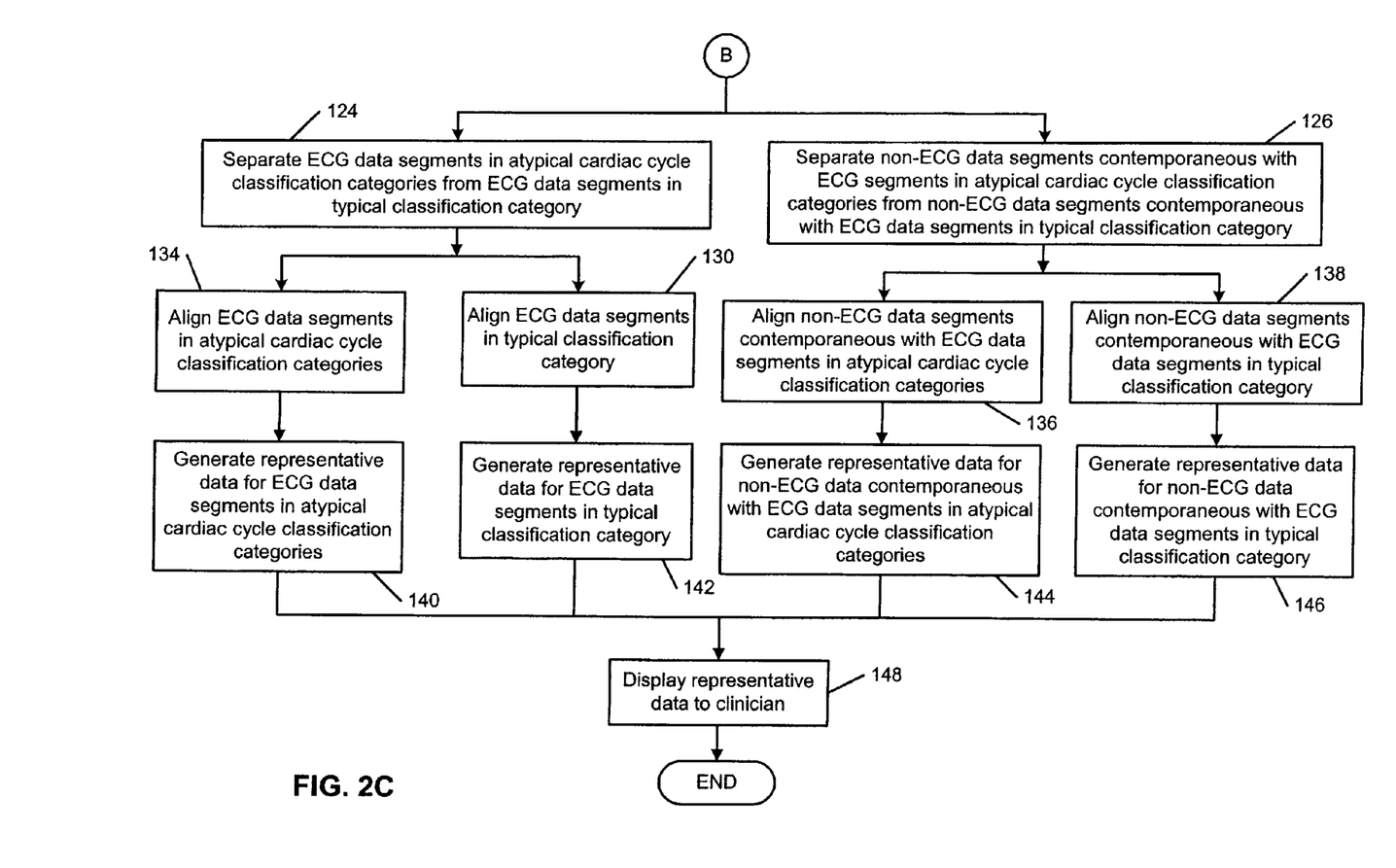

FIGS. 2A, 2B, and 2C illustrate a method of processing ECG data and non-ECG physiological data embodying the invention. Referring to FIG. 2A, non-ECG physiological data is acquired 100 from a patient, while ECG data is simultaneously acquired 102 from the patient. The non-ECG physiological data may include continuous blood pressure data, blood oxygen saturation data, cardiac impedance data, cardiac sound data, cardiac output data, cardiac imaging data, or any other physiological data.

Figure 3:
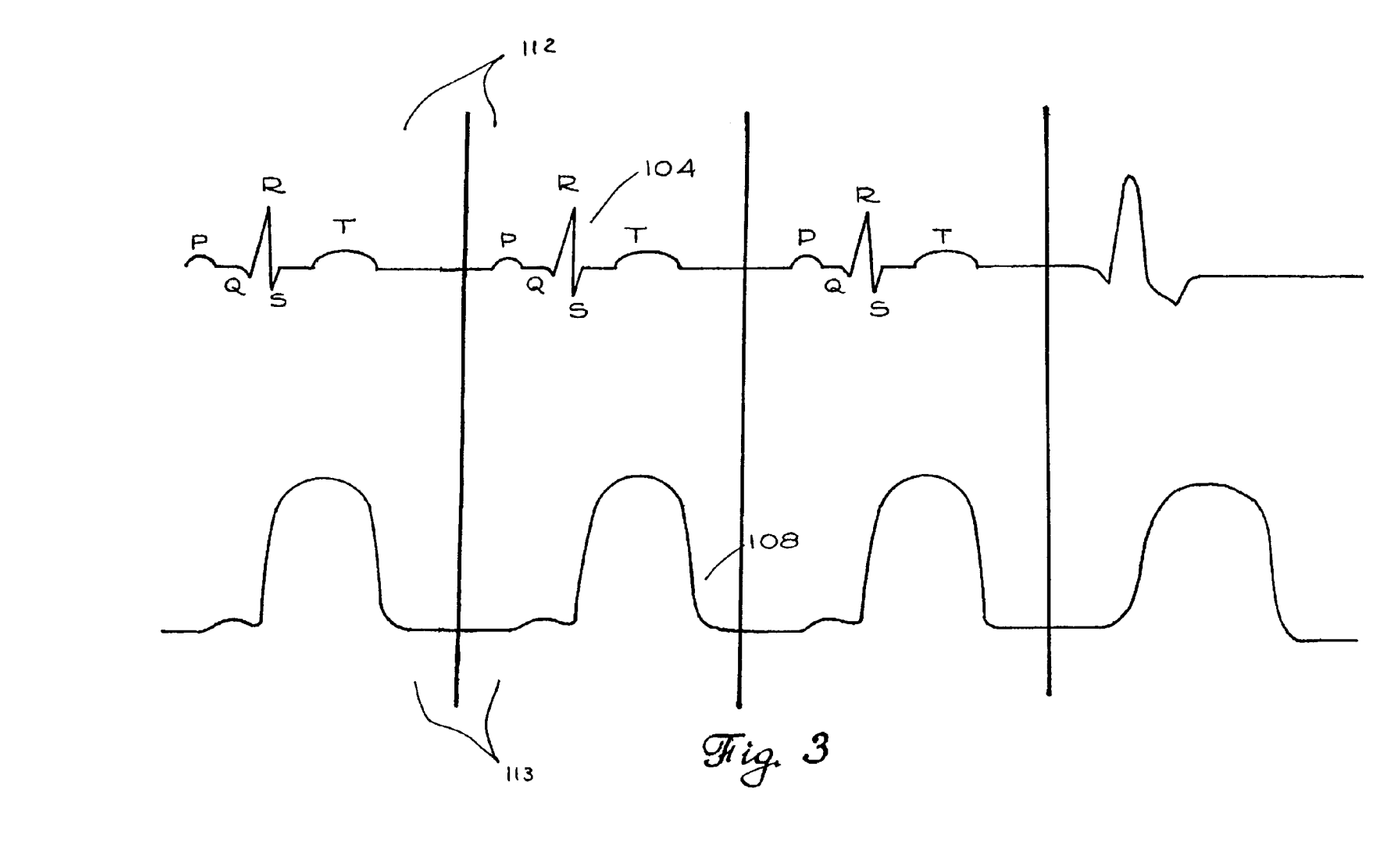
FIG. 3 illustrates simultaneously-acquired ECG and blood pressure waveforms.

FIG. 3 illustrates an ECG waveform 104 simultaneously acquired with a continuous blood pressure waveform 108. The ECG waveform 104 and the continuous blood pressure waveform 108, as illustrated in FIG. 3, each include four separate cardiac cycles.

Referring to FIG. 2A, the ECG waveforms are inputted 105 into an ECG classification engine. The ECG classification engine digitizes and samples 108 the waveforms to create ECG data. The ECG data is then initially filtered 109 to eliminate obvious noise, such as 50 or 60 Hertz power line interference.

Figure 4:
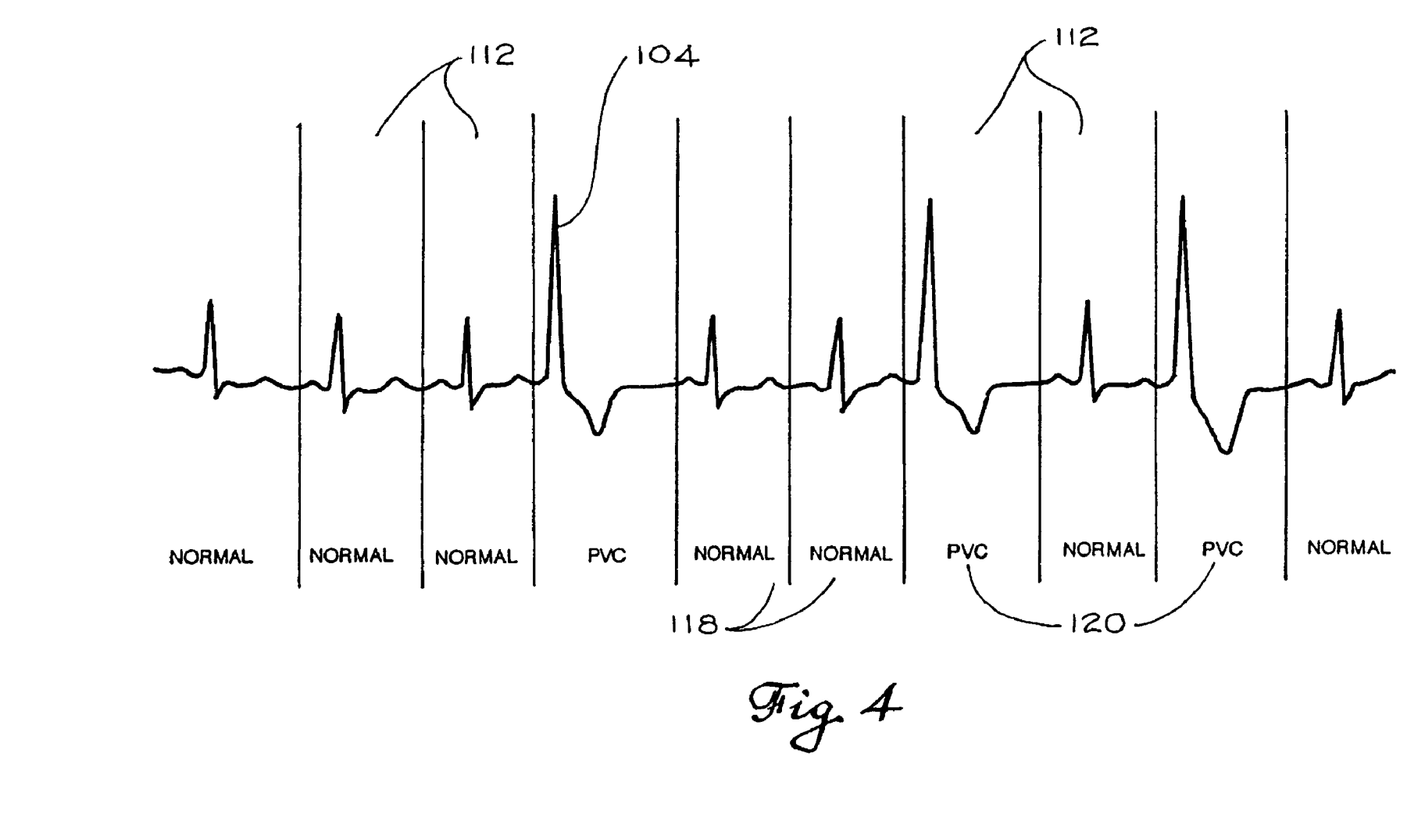
FIG. 4 illustrates a segmented ECG waveform with the segments designated as a normal cardiac cycle or a cardiac cycle associated with a premature ventricular contraction (PVC).

Once the ECG data is filtered 109, individual heart beats are detected 110 by locating the QRS complexes within the ECG data. The ECG data is then divided 114 into cardiac cycle segments corresponding to each of the individual QRS complexes. As illustrated in FIGS. 3 and 4, the ECG data 104 is divided 114 into a plurality of ECG data segments 112.

The ECG data 104 may be divided 114 into a plurality of ECG data segments 112 in the following manner. If 1000 samples of digitized ECG data are recorded at 100 samples per second, the samples represent 10 seconds of ECG waveform data. If 10 heart beats have occurred during this time, each heart beat or cardiac cycle includes about 100 samples. The heart beats are unlikely to each include exactly 100 samples, because the 10 heart beats will not, in general, have exactly the same period. Thus, the ECG data 104 is divided 114 into 10 ECG data segments 112 with each data segment 112 comprised of approximately 100 samples.

Once the ECG data is divided 114 into data segments 112, the non-ECG physiological data is divided 114 into a plurality of non-ECG physiological data segments 113 (illustrated in FIG. 3 as continuous blood pressure data segments) that are contemporaneous with the simultaneously-acquired ECG data segments 112. Preferably, each ECG data segment 112 and each non-ECG physiological data segment 113 represents a single cardiac cycle. However, the data may be divided or segmented in any manner suitable for the processing of the data.

Referring to FIGS. 2A, 2B, and 4, once the ECG data and the non-ECG physiological data are divided 114 into segments, the ECG data segments 112 are analyzed 116 in order to identify the ECG data segments 112 that are associated with atypical cardiac cycles. The term "atypical" is used to refer to any data segment having a morphology that differs from most of the other data segments. An atypical cardiac cycle may be considered a normal cardiac cycle, i.e. a cardiac cycle may differ from other cardiac cycles, but may not be related to a cardiac disease, malfunction, or abnormality. Several types of normal cardiac cycles may exist within a stream of ECG waveform data. However, each of these normal cardiac cycles differs from the typical cardiac cycles and is thus considered atypical. Cardiac cycles associated with abnormal cardiac cycles are referred to as ectopic or aberrant heart beats.

In order to identify 116 the ECG data segments 112 associated with atypical cardiac cycles, each of the ECG data segments 112 is compared to each one of a plurality of templates stored within the ECG classification engine. The plurality of stored templates corresponds to an extensive list of types of cardiac cycles. Each stored template corresponds to one type of cardiac cycle. Each stored template includes a set of sample values representing a typical cardiac cycle associated with that particular cardiac cycle. To compare an ECG data segment 112 with a stored template, each sample of the ECG data segment 112 is compared with each sample of the template to determine if the ECG data segment 112 is substantially similar to the template.

If the ECG data segment 112 is substantially similar to one of the plurality of stored templates, the ECG data segment 112 is identified 116 as being associated with the cardiac cycle designated by the template. If none of the plurality of stored templates is substantially similar to the ECG data segment 112, the ECG data segment 112 is used to form a new template. The new template is stored within the ECG classification engine and compared to future ECG data segments in a similar manner.

After being compared to the plurality of stored templates, the ECG data segments 112 are identified 116 as either associated with a typical cardiac cycle or as associated with specific atypical cardiac cycle. In the ECG data illustrated in FIG. 4, several ECG data segments 112 are identified 116 as being associated with a normal or typical cardiac cycle 118 and several ECG data segments 112 are identified 116 as being associated with a premature ventricular contraction (PVC) cardiac cycle 120.

As illustrated in FIG. 4, the QRS complexes in the PVC cardiac cycles 120 are usually greater than 120 milliseconds in duration, while the QRS complexes in the normal or typical cardiac cycles 118 are usually only 100 milliseconds in duration. Moreover, the QRS complexes in PVC cardiac cycles 120 are greater in amplitude than the QRS complexes in the normal or typical cardiac cycles 118.

Once the ECG data segments 112 associated with the atypical cardiac cycles are identified 116, the ECG data segments 112 may be analyzed in the context of the surrounding ECG data segments 112 in order to analyze the rhythm of the entire set of ECG data. For example, an isolated PVC cardiac cycle 120 surrounded by normal or typical cardiac cycles 118 may have little clinical significance. However, a long string of PVC cardiac cycles 120 indicates ventricular tachycardia, which is a serious, possibly lethal, cardiac condition.

Referring to FIGS. 2B, 3, and 4, once the ECG data segments 112 associated with the atypical cardiac cycles are identified 116, the non-ECG physiological data segments 113 that were simultaneously acquired with those ECG data segments 112 are also identified 121. In this manner, the ECG data segments 112 associated with the atypical cardiac cycles and the contemporaneous non-ECG physiological data segments 113 associated with the atypical cardiac cycles are both identified 121 and associated with one another.

Each one of the plurality of templates stored within the ECG classification engine is associated with one of several broader classification categories. Thus, each one of the cardiac cycles designated by each one of the plurality of stored templates is associated with a classification category, i.e. a broad category of cardiac events associated with several of the stored templates.

In one embodiment, each one of the plurality of stored templates is associated with one of ten classification categories. Specifically, the ten classification categories are as follows: (1) typical QRS, (2) atrial artificially paced typical QRS, (3) premature supraventricular QRS, (4) ventricular artificially paced QRS, (5) premature ventricular QRS, (6) T wave, (7) P wave, (8) ventricular artificial pacing spike, (9) atrial artificial pacing spike, and (10) artifact. Classification categories 1 through 5 are all legitimate QRS complex detections. Classification categories 6 through 10 are detections that are not based on the QRS complex.

In another embodiment, the stored templates are associated with one of five broader classification categories. Specifically, the five classification categories are as follows: (1) normal, (2) premature supraventricular (PSV), (3) premature ventricular contraction (PVC), (4) atrial paced, and (5) ventricular paced. The five classification categories are broader than the ten classification categories described above.

Referring to FIGS. 2B, 3, and 4, the ECG classification engine determines 122 which classification category the ECG data segment 112 is associated with according to which one of the plurality of stored templates is associated with the ECG data segment 112. The ECG classification engine then labels 123 each ECG data segment 112 and each non-ECG physiological data segment 113 with one of the above-described classification categories.

In the preferred embodiment of the invention, once both the ECG data segments 112 and the non-ECG data segments 113 associated with the atypical cardiac cycles have been identified and categorized, the data segments associated with the atypical cardiac cycles are separated from the data segments associated with the typical cardiac cycles. Separating the data segments associated with the atypical cardiac cycle from the data segments associated with the typical cardiac cycle is achieved in one of two ways. The data segments are preferably separated according to which one of the classification categories each data segment is associated with. Alternatively, the data segments are separated according to which one of the plurality of stored templates each data segment is associated with.

Specifically, referring to FIGS. 2C, 3, and 4, the ECG data segments 112 in the atypical cardiac cycle classification categories are separated 124 from the ECG data segments 112 in the typical classification category. Similarly, the non-ECG data segments 113 that are contemporaneous with the ECG data segments 112 in the atypical cardiac cycle classification categories are separated 126 from the non-ECG data segments 113 contemporaneous with the ECG data segments 112 in the typical classification category. The data segments may be separated by placing each classification category of data segments into separate memory locations accessible by the software.

Once the data segments are separated according to classification category, the data segments within each individual classification category are combined. In order to coherently combine the data segments, the data segments must be accurately aligned.

Figure 5:
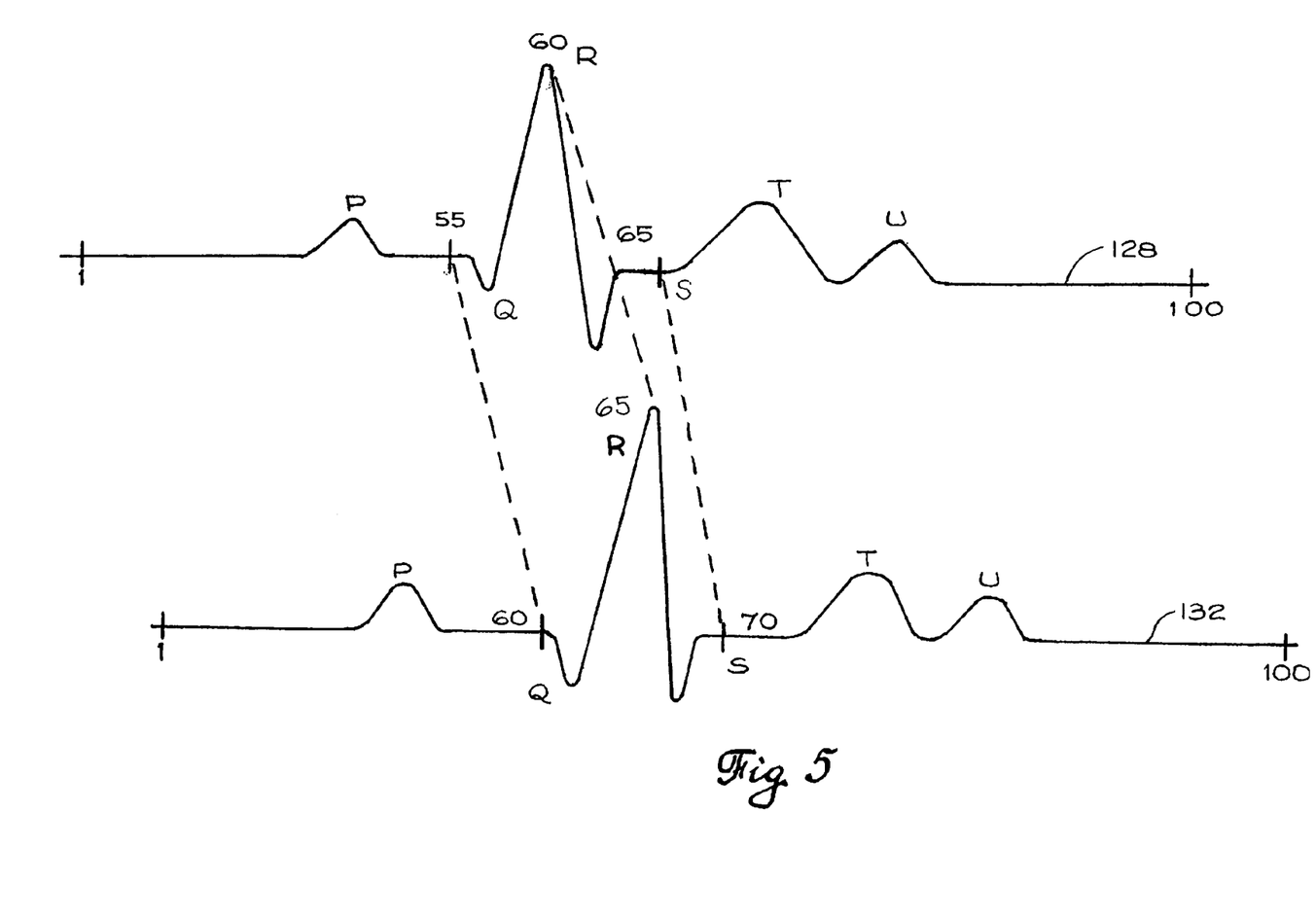
FIG. 5 illustrates the alignment of two ECG waveforms based on the QRS complex as a fiducial point.

As shown in FIG. 5, the ECG data segments in the typical classification category are aligned. Referring to FIGS. 2C and 5, a first ECG data segment 128 is temporally aligned 130 with a second ECG data segment 132. For example, the first ECG data segment 128 and the second ECG data segment 132 may each include about 100 samples, i.e. 100 data points representing a portion of the ECG waveform. Each of the 100 samples is numbered so that the first sample of each set is numbered 1, the second sample is numbered 2, and so on. In the first ECG data segment 128, the feature to be used as a fiducial point is the QRS complex which occurs in the segment 128 between samples 55 and 65. In the second ECG data segment 132, the QRS complex occurs between samples 60 and 70. In order to align the segments to compare the QRS complexes of the segments, sample 55 of segment 128 is aligned with sample 60 of segment 132, sample 60 of segment 128 is aligned with sample 65 of segment 132, and sample 65 of segment 128 is aligned with sample of 70 of segment 132. The samples are aligned in this manner rather than simply aligning sample 55 of segment 128 with sample 55 of segment 132, and so on. In the preferred embodiment of the invention, the QRS complex of the first ECG data segment 128 is accurately aligned 130 within one sample, out of the 100 samples, of the QRS complex of the second ECG data segment 132.

Referring to FIGS. 2C and 4, in a similar manner as described above, the ECG data segments 112 in the classification categories associated with atypical cardiac cycles are aligned 134. The fiducial points within the ECG data segments associated with the atypical cardiac cycles are identified by the ECG classification engine. Once the fiducial points are identified, the ECG data segments 112 are aligned in the same manner as the ECG data segments 112 in the typical classification category, as shown in FIG. 5 and described above. For example, the QRS complex in the PVC cardiac cycles 120, although abnormal, can still serve as a fiducial point to align the data segments in the PVC classification category.

Referring to FIGS. 2C and 3, by relying on the QRS complex of the simultaneously-acquired ECG data segments 112, the non-ECG data segments 113 contemporaneous with the ECG data segments 112 in the typical classification category are aligned 138, and the non-ECG data segments 113 contemporaneous with the ECG data segments 112 in the classification categories associated with atypical cardiac cycles are aligned 136. Specifically, once the ECG data segments 112 in the typical classification category are aligned, the non-ECG data segments 113 in the typical classification category are temporally aligned 138 in the same manner as the ECG data segments 112 in the typical classification category.

For example, referring to FIG. 5, if sample 55 of the first ECG data segment 128 and sample 60 of the second ECG data segment 132 are aligned, then sample 55 of the non-ECG physiological data segment associated with segment 128 and sample 60 of the non-ECG physiological data segment associated with segment 132 are aligned. In the same manner, once the ECG data segments 112 in the atypical cardiac cycle classification categories are aligned, the non-ECG data segments 113 in the atypical cardiac cycle classification categories are temporally aligned 136 in the same manner as the ECG data segments 112 in the atypical cardiac cycle classification categories.

Once the data segments in each of the classification categories are aligned, representative data for each of the classification categories is generated by combining the data segments within each classification category. To combine the data segments, each sample in each data segment is averaged with the samples that it is aligned with from all the other data segments in order to generate one average sample. For example, referring to FIG. 5, if sample 55 of segment 128 is aligned with sample 60 of segment 132, sample 55 and sample 60 are averaged to generate a single sample representing both segments. All of the averaged samples taken together then form the representative data for the classification category.

Alternatively, to combine the data segments, a median sample can be determined for the samples that are aligned together. All of the median samples taken together then form the representative data for the classification category.

In the preferred embodiment of the invention, at least two separate sets of representative data are generated. For example, if no atypical cardiac cycles occur within the ECG data segments 112, as few as two sets of representative data are generated, namely one ECG data segment representing the typical classification category and one non-ECG data segment representing the typical classification category. However, more than one type of non-ECG physiological data may be gathered. If no atypical cardiac cycles occur within the ECG data segments 112, but more than one type of non-ECG physiological data is gathered, one set of representative data is generated to represent the typical classification categories associated with each type of non-ECG physiological data that is acquired, along with one set of representative data for the typical ECG classification category.

If an atypical cardiac cycle does occur within the ECG data segments 112, representative data is generated for both the typical classification category and the atypical cardiac cycle classification category for each type of non-ECG physiological data, along with representative data for the typical and atypical ECG classification categories. Moreover, if more than one type of atypical cardiac cycle occurs, representative data is generated for each of the atypical cardiac cycle classification categories associated with each type of non-ECG physiological data that is acquired.

Referring to FIGS. 2C, 3, and 4, representative data for the ECG data segments 112 in the atypical cardiac cycle classification categories is generated 140 and representative data for the ECG data segments 112 in the typical classification category is generated 142. In a similar manner, representative data for the non-ECG physiological data segments 113 that are contemporaneous with the ECG data segments 112 in the atypical cardiac cycle classification categories is generated 144, and representative data for the non-ECG physiological data segments 113 that are contemporaneous with the ECG data segments 112 in the typical classification category is generated 146.

Several types of non-ECG physiological data may be acquired, along with the ECG data. Moreover, several types of atypical cardiac cycles may occur while the data is being acquired. For example, if continuous blood pressure data, X-ray imaging data, and ECG data are acquired, and premature ventricular contractions (PVC) and premature supraventricular contractions (PSV) occur during the data acquisition, nine sets of representative data are generated. The nine sets of representative data are: (1) typical continuous blood pressure, (2) PVC continuous blood pressure, (3) PSV continuous blood pressure, (4) typical X-ray, (5) PVC X-ray, (6) PSV X-ray, (7) typical ECG, (8) PVC ECG, and (9) PSV ECG.

Figure 6:
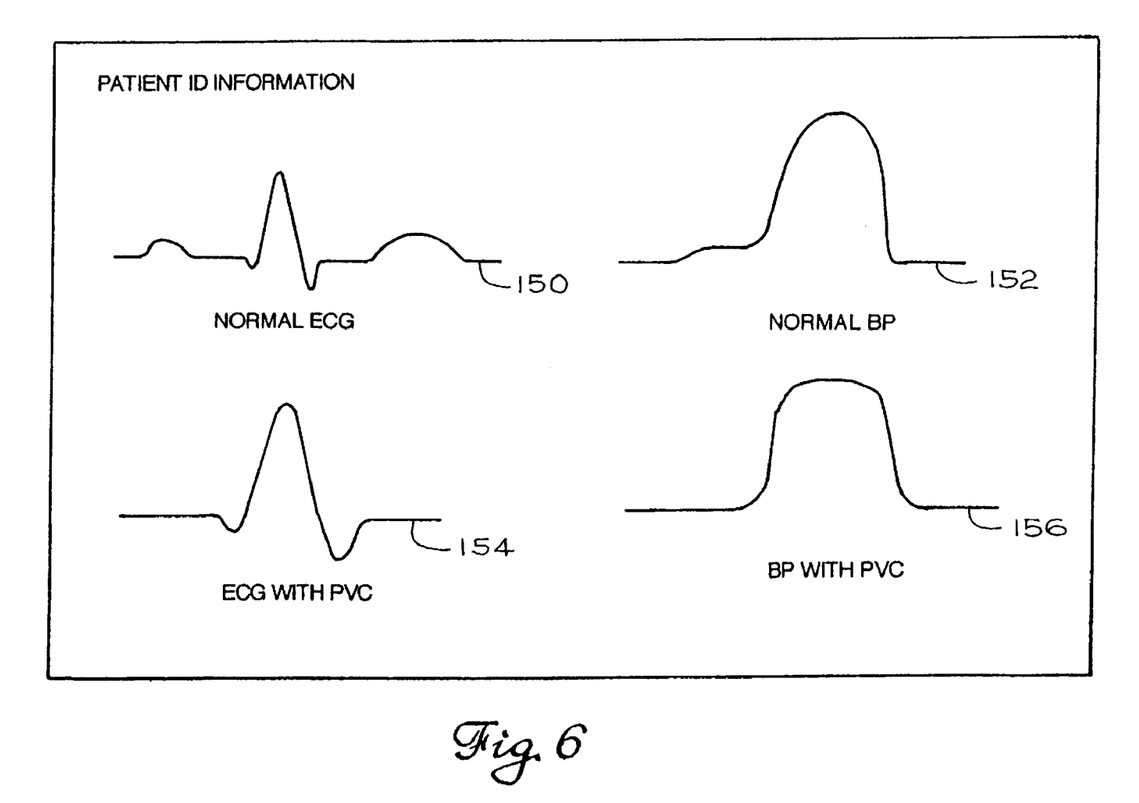
FIG. 6 illustrates a display including four sets of representative data.

As illustrated in FIGS. 2C and 6, four separate sets of representative data may be displayed 148 to a clinician on a display monitor coupled to the clinical device. The display in FIG. 6 includes two ECG waveforms and two continuous blood pressure waveforms. Specifically, representative data for the ECG data in the typical classification category 150 is displayed, and representative data for the ECG data in the PVC classification category 154 is displayed. In addition, representative data for the continuous blood pressure data in the typical classification category 152 is displayed, and representative data for the continuous blood pressure data in the PVC classification category 156 is displayed.

The representative data for the atypical cardiac cycle classification categories is particularly useful to clinicians, because the cardiac cycles associated with the atypical cardiac cycles are often more clinically significant than the typical cardiac cycles. Thus, the representative data for the non-ECG physiological data in the atypical cardiac cycle classification categories may be even more valuable to clinicians than the representative data for the non-ECG physiological data in the typical classification category. Separating the data segments in the atypical cardiac cycle classification categories from the data segments in the typical classification category also prevents the data segments in the typical classification category from suffering any accumulated negative effect from being averaged or combined with distorted data segments.

In another preferred embodiment, the representative data is transmitted from the clinical device to a remote location. Generating representative data based on acquired data is a method of compressing data, because the representative data is a much smaller set of data than the acquired data. Accordingly, the memory required to store the representative data and the bandwidth required to transmit the representative data is less than the memory required to store the acquired data and the bandwidth required to transmit the acquired data. Since the bandwidth required to transmit the representative data is less than the bandwidth required to transmit the acquired data, the representative data is transmitted from the clinical device to any type of device located remotely from the clinical device. By way of example only, the representative data may be transmitted from the clinical device to a remote device via phone lines, the internet, wireless communication devices, or any other type of data transmission devices. Various features and advantages of the invention are set forth in the following claims.

What is claimed is:

1. A method of processing physiological data acquired from a patient, the method comprising the acts of:

acquiring a first type of physiological data and a second type of physiological data from the patient;

dividing the first type of physiological data and the second type of physiological data into corresponding segments;

analyzing the first type of physiological data segments to determine the morphology of each data segment;

clustering the data segments of the first type of physiological data into atypical and typical groups based on the morphology of each data segment;

clustering the data segments of the second type of physiological data into atypical and typical groups based on the corresponding segments of the first type of physiological data; and generating representative data for at least one of the atypical groups of the data segments of the first type of physiological data and the atypical groups of the data segments of the second type of physiological data.

2. The method of claim 1 wherein the act of acquiring a first type of physiological data includes the act of acquiring electrocardiogram data.

3. The method of claim 1 wherein the act of acquiring a second type of physiological data includes the act of acquiring at least one of blood pressure data, blood oxygen saturation data, cardiac output data, cardiac impedance data, cardiac sounds data, and cardiac imaging data.

4. The method of claim 1 wherein the act of dividing the first type of physiological data and the second type of physiological data into corresponding segments includes the act of dividing the first type of physiological data and the second type of physiological data into data segments corresponding to cardiac cycles.

5. The method of claim 1 and further comprising the act of categorizing the first type of physiological data segments using an electrocardiogram classification engine.

6. The method of claim 5 wherein the act of categorizing the first type of physiological data segments using an electrocardiogram classification engine includes the act of categorizing the data segments into classification categories associated with at least one of a typical cardiac cycle, a premature supraventricular cardiac cycle, a premature ventricular contraction cardiac cycle, an atrial paced cardiac cycle, and a ventricular paced cardiac cycle.

7. The method of claim 5 wherein the act of categorizing the first type of physiological data segments using an electrocardiogram classification engine includes the act of categorizing the data segments into classification categories based on the morphology of the data segment and the morphology of adjacent data segments.

8. The method of claim 1 and further comprising the act of separating the groups of data segments from one another.

9. The method of claim 8 and further comprising the act of aligning the groups of data segments according to a fiducial point.

10. The method of claim 9 wherein the fiducial point further comprises a plurality of data samples and wherein the act of aligning the separated segments includes the act of aligning the data samples of the fiducial point.

11. The method of claim 9 wherein the fiducial point is the QRS complex.

12. The method of claim 1 and further comprising the act of generating representative data for at least one of the typical groups of the data segments of the first type of physiological data and the typical groups of the data segments of the second type of physiological data.

13. The method of claim 1 wherein the act of generating representative data for the groups of data segments includes the act of averaging the data segments.

14. The method of claim 1 wherein the act of generating representative data for the groups of data segments includes the act of determining a median data segment.

15. The method of claim 1 and further comprising the act of transmitting the representative data to a remote location.

16. The method of claim 1 and further comprising the act of displaying the representative data to a clinician.

17. A method of processing physiological data acquired from a patient, the method comprising the acts of:

acquiring electrocardiogram data and non-electrocardiogram physiological data from the patient;

dividing the electrocardiogram data and the non-electrocardiogram physiological data into corresponding segments;

analyzing the electrocardiogram data segments to identify atypical and typical segments;

associating the atypical electrocardiogram data segments with the corresponding non-electrocardiogram physiological data segments;

associating the typical electrocardiogram data segments with the corresponding non-electrocardiogram physiological data segments; and generating representative data for at least the atypical electrocardiogram data segments.

18. The method of claim 17 wherein the act of acquiring non-electrocardiogram cardiac data includes the act of acquiring at least one of a blood pressure data, a blood oxygen saturation data, a cardiac output data, a cardiac impedance data, a cardiac sounds data, and cardiac imaging data.

19. The method of claim 17 wherein the act of dividing the electrocardiogram data and the non-electrocardiogram physiological data into corresponding segments includes the act of dividing the electrocardiogram data and the non-ECG physiological data into data segments corresponding to cardiac cycles.

20. The method of claim 17 wherein the act of analyzing the electrocardiogram data segments to identify atypical and typical segments includes the act of categorizing the electrocardiogram data segments using an electrocardiogram classification engine.

21. The method of claim 20 wherein the act of categorizing the data segments using an electrocardiogram classification engine includes the act of categorizing the electrocardiogram data segments into classification categories associated with at least one of a typical cardiac cycle, a premature supraventricular cardiac cycle, a premature ventricular contraction cardiac cycle, an atrial paced cardiac cycle, and a ventricular paced cardiac cycle.

22. The method of claim 20 wherein the act of categorizing the electrocardiogram data segments using an electrocardiogram classification engine includes the act of categorizing the electrocardiogram data segments into classification categories based on the morphology of the data segment and the morphology of adjacent data segments.

23. The method of claim 17 and further comprising the act of separating the atypical electrocardiogram data segments from the typical electrocardiogram data segments.

24. The method of claim 23 and further comprising the act of separating the non-electrocardiogram physiological data segments associated with the atypical electrocardiogram data segments from the non-electrocardiogram physiological data segments associated with the typical electrocardiogram data segments.

25. The method of claim 24 and further comprising the act of aligning the separated data segments according to a fiducial point.

26. The method of claim 25 wherein the fiducial point further comprises a plurality of data samples and wherein the act of aligning the data segments includes the act of aligning the data samples of the fiducial point.

27. The method of claim 25 wherein the fiducial point is the QRS complex.

28. The method of claim 17 and further comprising the act of generating representative data for at least one of the non-electrocardiogram data segments corresponding to the atypical electrocardiogram data segments, the typical electrocardiogram data segments, and the non-electrocardiogram data segments corresponding to the typical electrocardiogram data segments.

29. The method of claim 17 wherein the act of generating representative data includes the act of averaging the separated data segments.

30. The method of claim 17 wherein the act of generating representative data includes the act of determining a median data segment.

31. The method of claim 17 and further comprising the act of transmitting the representative data to a remote location.

32. The method of claim 17 and further comprising the act of displaying the representative data to a clinician.

33. A method of processing physiological data acquired from a patient, the method comprising the acts of:

acquiring electrocardiogram data and non-electrocardiogram physiological data from the patient;

dividing the electrocardiogram data and the non-electrocardiogram physiological data into corresponding segments;

providing an electrocardiogram classification engine;

inputting the electrocardiogram data segments into the electrocardiogram classification engine;

classifying the electrocardiogram data segments in order to identify atypical and typical electrocardiogram data segments;

associating the atypical electrocardiogram data segments with the corresponding non-electrocardiogram physiological data segments;

associating the typical electrocardiogram data segments with the corresponding non-electrocardiogram physiological data segments; and generating representative data for at least one of the atypical electrocardiogram data segments and for the corresponding non-electrocardiogram data segments.

34. The method of claim 33 wherein the act of acquiring non-electrocardiogram physiological data includes the act of acquiring at least one of a blood pressure data, a blood oxygen saturation data, a cardiac output data, a cardiac impedance data, a cardiac sounds data, and cardiac imaging data.

35. The method of claim 33 wherein the act of dividing the electrocardiogram data and the non-electrocardiogram physiological data into corresponding segments includes the act of dividing the electrocardiogram data and the non-electrocardiogram physiological data into segments corresponding to cardiac cycles.

36. The method of claim 33 wherein the act of classifying the electrocardiogram data segments includes the act of categorizing the segments into classification categories associated with at least one of atypical cardiac cycle, a premature supraventricular cardiac cycle, a premature ventricular contraction cardiac cycle, an atrial paced cardiac cycle, and a ventricular paced cardiac cycle.

37. The method of claim 33 wherein the act of categorizing the electrocardiogram data segments using an electrocardiogram classification engine includes the act of categorizing the data segments into classification categories based on the morphology of the data segment and the morphology of adjacent data segments.

38. The method of claim 33 and further comprising the act of separating the atypical electrocardiogram data segments from the typical electrocardiogram data segments.

39. The method of claim 38 and further comprising the act of separating the non-electrocardiogram physiological data segments associated with the atypical electrocardiogram data segments from the non-electrocardiogram physiological data segments associated with the typical electrocardiogram data segments.

40. The method of claim 39 and further comprising the act of aligning the separated data segments according to a fiducial point.

41. The method of claim 39 wherein the fiducial point further comprises a plurality of data samples and wherein the act of aligning the separated data segments includes the act of aligning the data samples of the fiducial point.

42. The method of claim 39 wherein the fiducial point is the QRS complex.

43. The method of claim 33 and further comprising the act of generating representative data for at least one of the typical electrocardiogram data segments and for the corresponding non-electrocardiogram data segments.

44. The method of claim 33 wherein the act of generating representative data includes the act of averaging the separated data segments.

45. The method of claim 33 wherein the act of generating representative data includes the act of determining a median data segment.

46. The method of claim 33 and further comprising the act of transmitting the representative data to a remote location.

47. The method of claim 33 and further comprising the act of displaying the representative data to a clinician.

48. A method of processing physiological data acquired from a patient, the method comprising the acts of:

acquiring electrocardiogram data and non-electrocardiogram physiological data from the patient;

dividing the electrocardiogram data and the non-electrocardiogram physiological data into data segments so that each electrocardiogram data segment is associated with one non-electrocardiogram physiological data segment;

analyzing the electrocardiogram data segments to identify the morphology of each electrocardiogram data segment;

clustering the electrocardiogram data segments into atypical and typical groups based on the morphology of each electrocardiogram data segment;

clustering the non-electrocardiogram physiological data segments into atypical and typical groups based on the electrocardiogram data segment associated with each non-electrocardiogram physiological data segment; and generating representative data for at least one of the atypical groups of the electrocardiogram data segments and the atypical groups of the non-electrocardiogram physiological data segments.

49. The method of claim 48 wherein the act of acquiring non-electrocardiogram cardiac data includes the act of acquiring at least one of a blood pressure data, a blood oxygen saturation data, a cardiac output data, a cardiac impedance data, a cardiac sounds data, and cardiac imaging data.

50. The method of claim 48 wherein the act of dividing the electrocardiogram data and the non-electrocardiogram physiological data into corresponding segments includes the act of dividing the electrocardiogram data and the non-electrocardiogram physiological data into data segments corresponding to cardiac cycles.

51. The method of claim 48 and further comprising the act of categorizing the electrocardiogram data segments using an electrocardiogram classification engine.

52. The method of claim 51 wherein the act of categorizing the electrocardiogram data segments includes the act of categorizing the segments into classification categories associated with at least one of atypical cardiac cycle, a premature supraventricular cardiac cycle, a premature ventricular contraction cardiac cycle, an atrial paced cardiac cycle, and a ventricular paced cardiac cycle.

53. The method of claim 51 wherein the act of categorizing the electrocardiogram data segments using an electrocardiogram classification engine includes the act of categorizing the data segments into classification categories based on the morphology of the data segment and the morphology of adjacent data segments.

54. The method of claim 48 and further comprising the act of separating the groups of data segments from one another.

55. The method of claim 54 and further comprising the act of aligning the data segments according to a fiducial point.

56. The method of claim 55 wherein the fiducial point further comprises a plurality of data samples and wherein the act of aligning the data segments includes the act of aligning the data samples of the fiducial point.

57. The method of claim 55 wherein the fiducial point is the QRS complex.

58. The method of claim 48 and further comprising the act of generating representative data for at least one of the typical groups of the electrocardiogram data segments and the typical groups of the non-electrocardiogram physiological data segments.

59. The method of claim 48 wherein the act of generating representative data for the groups of data segments includes the act of averaging the data segments.

60. The method of claim 48 wherein the act of generating representative data for the groups of data segments includes the act of determining a median data segment.

61. The method of claim 48 and further comprising the act of transmitting the representative data to a remote location.

62. The method of claim 48 and further comprising the act of displaying the representative data to a clinician.

63. A clinical device coupleable to a patient comprising:
an acquisition module for acquiring electrocardiogram data and non-electrocardiogram physiological data from the patient; and
a computer-readable medium encoded with software for
dividing the electrocardiogram data and the non-electrocardiogram physiological data into corresponding segments,
analyzing the electrocardiogram data segments to identify atypical and typical segments,
associating the atypical electrocardiogram data segments with the corresponding non-electrocardiogram physiological data segments,
associating the typical electrocardiogram data segments with the corresponding non-electrocardiogram physiological data segments, and
generating representative data for at least one of the atypical electrocardiogram data segments and the corresponding non-electrocardiogram data segments.

64. The clinical device of claim 63 wherein the non-electrocardiogram physiological data includes at least one of a blood pressure data, a blood oxygen saturation data, a cardiac output data, a cardiac impedance data, a cardiac sounds data, and cardiac imaging data.

65. The clinical device of claim 63 wherein the data segments correspond to cardiac cycles.

66. The clinical device of claim 63 wherein the software includes an electrocardiogram classification engine.

67. The clinical device of claim 66 wherein the software categorizes the data segments into classification categories associated with at least one of a typical cardiac cycle, a premature supraventricular contraction cardiac cycle, a premature ventricular contraction cardiac cycle, and an atrial paced cardiac cycle, and a ventricular paced cardiac cycle.

68. The clinical device of claim 66 wherein the software categorizes the data segments into classification categories based on the morphology of the data segment and the morphology of adjacent data segments.

69. The clinical device of claim 63 wherein the software separates the atypical electrocardiogram data segments from the typical electrocardiogram data segments.

70. The clinical device of claim 69 wherein the software separates the non-electrocardiogram physiological data segments associated with the atypical electrocardiogram data segments from the non-electrocardiogram physiological data segments associated with the typical electrocardiogram data segments.

71. The clinical device of claim 70 wherein the software aligns the segments according to a fiducial point.

72. The clinical device of claim 71 wherein the fiducial point further comprises a plurality of data samples and wherein the software aligns the data samples of the fiducial point.

73. The clinical device of claim 71 wherein the fiducial point is the QRS complex.

74. The clinical device of claim 63 wherein the software generates representative data for at least one of the typical electrocardiogram data segments and for the corresponding non-electrocardiogram data segments.

75. The clinical device of claim 63 wherein the software generates representative data by averaging the separated data segments.

76. The clinical device of claim 63 wherein the software generates representative data by determining a median data segment.

77. The clinical device of claim 63 wherein the software transmits the representative data to a remote location.

78. The clinical device of claim 63 and further comprising a display monitor for displaying the representative data to a clinician.

* * * * *